(12) United States Patent  (10) Patent No.: US 8,365,577 B2
Seeck et al.  (45) Date of Patent: Feb. 5, 2013

(54) DEVICE FOR SELECTIVELY DETERMINING THE QUANTITY OF OIL MIST OR AEROSOLS

(75) Inventors: Andreas Seeck, Lübeck (DE); Andreas Mohrmann, Krummesse (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 294 days.

(21) Appl. No.: 12/843,187

(22) Filed: Jul. 26, 2010

(65) Prior Publication Data

US 2011/0088454 A1  Apr. 21, 2011

(30) Foreign Application Priority Data

Oct. 17, 2009  (DE) .......................... 10 2009 049 768
Mar. 4, 2010  (DE) .......................... 10 2010 010 112

(51) Int. Cl.
*G01N 37/00* (2006.01)
*G01D 11/24* (2006.01)

(52) U.S. Cl. ........................................ 73/28.01; 73/431

(58) Field of Classification Search ................. 73/28.01, 73/29.01, 29.04, 431, 19.01
See application file for complete search history.

(56) References Cited

U.S. PATENT DOCUMENTS 4,868,398 A * 9/1989 Mulcey et al. ............. 250/458.1
7,712,348 B2  5/2010 Luebbert et al.
2006/0049346 A1* 3/2006 McGann et al. ............. 250/287

FOREIGN PATENT DOCUMENTS

DE  102006023714  11/2007
GB  2438217 A  11/2007
WO  WO 03/081212 A2  10/2003
WO  WO 2007/011726 A1  1/2007

* cited by examiner

*Primary Examiner* — Hezron E Williams
*Assistant Examiner* — David Z Huang
(74) *Attorney, Agent, or Firm* — McGlew and Tuttle, P.C.

(57) ABSTRACT

A measuring sensor (1) for the selective determination of oil mist or aerosols makes possible gas analysis in the ambient air. The measuring sensor (1) is inserted into an adapter housing (11), and a vacuum, by which ambient air is drawn in via the gas inlet duct (8) of the measuring sensor (1), is generated in the adapter housing (11) by means of a gas delivery pump (15).

9 Claims, 2 Drawing Sheets

DEVICE FOR SELECTIVELY DETERMINING THE QUANTITY OF OIL MIST OR AEROSOLS

CROSS REFERENCE TO RELATED APPLICATIONS

This application claims the benefit of priority under 35 U.S.C. §119 of German Patent Application DE 10 2009 049 768.4 filed Oct. 17, 2009 and German Patent Application DE 10 2010 010 112.5 filed Mar. 4, 2010, the entire contents of each of which are incorporated herein by reference.

FIELD OF THE INVENTION

The present invention pertains to a device for selectively determining the quantity of oil mist or aerosols in a gas sample.

BACKGROUND OF THE INVENTION

A device for selectively determining the quantity of mist is known from DE 10 2006 023 714 B4. The prior-art measuring sensor is based on the so-called impactor principle, in which an air jet loaded with oil mist or aerosols is suddenly deflected in order to collect the deposited oil particles or aerosol particles on a deflector. The gas sample to be analyzed now flows through a plurality of micronozzles, which are arranged in a circle and whose diameter is selected to be such that a predetermined test gas flow will become established. The micronozzles are arranged in this case at the end of a gas inlet duct, and the deflector, at which the oil or aerosol particles are deposited, is located opposite the micronozzles. The quantity of oil or aerosol particles collected during a certain measurement time is an indicator of the oil or aerosol content in the gas sample.

The gas sample to be analyzed is usually taken from a pressure source, e.g., a central compressed air supply system in order to make it possible to carry out the gas analysis. The gas inlet duct of the measuring sensor is connected for this to the gas source via a connecting branch, and the micronozzles act as nozzles to which supercritical gas flow is admitted and they limit the flow quantity.

The drawback of the prior-art measuring sensor is that the gas analysis can be only carried out on a pressurized gas reservoir, whereas detection of oil mist or aerosols in the ambient air is not possible.

SUMMARY OF THE INVENTION

The basic object of the present invention is to improve a measuring sensor of the type mentioned such that oil mist or aerosols can be detected in the ambient air.

According to the invention, a device is provided for the selective determination of the quantity of oil mist or aerosols in a gas sample. The device comprises a measuring sensor with a micronozzle for dispensing a predetermined sample gas flow in a gas inlet chamber and a deflector downstream of the micronozzle for depositing aerosol or oil particles and a gas outlet on the discharge side of the deflector. An adapter housing at least partially encapsulates the measuring sensor. The adapter housing has a connecting branch for receiving the gas inlet duct and a pump port connected to the gas outlet establishing a flow connection via the gas inlet duct from the outside of the adapter housing to the pump port.

A gas delivery pump is connected to the pump port.

The adapter housing comprises a bottom part with the connecting branch and the pump port and a cover pulled over the free end of the bottom part. The cover may be provided with a window in the area of deflector.

The advantage of the device according to the present invention can be seen in the fact that the prior-art measuring sensor, which is designed for the gas analysis of a pressurized gas source, is inserted into an adapter housing in order to generate a test gas flow through the measuring sensor by means of a vacuum source. The adapter housing has a pump port for this, to which either an electrically driven pump or a hand-operated gas delivery pump can be connected. The test gas is drawn through the measuring sensor with the gas delivery pump. Commercially available gas delivery pumps, as they are known in connection with gas sampling in gas testing tubes, may be used for this.

A preferred average gas flow for gas sampling equals about 4 L/minute. The prior-art measuring sensor can thus be used, without any modifications having to be made, both for the gas analysis of compressed air sources and for the analysis of the ambient atmosphere. Only the prior-art measuring sensor is inserted into an adapter housing during the analysis of the ambient air and the sample gas flow is generated by means of a vacuum source, by which the test gas is drawn through the micronozzle of the measuring sensor.

The adapter housing advantageously comprises a bottom unit with a connecting branch for receiving a gas inlet duct of the measuring sensor as well as a pump port for the gas delivery pump. The gas inlet duct of the measuring sensor is attached in the connecting branch such that ambient air can be drawn in directly via its free end. The free end of the bottom part is closed with a cover, and a window, which is located opposite the deflector of the measuring sensor, is arranged on the top side of the cover. The loading of the deflector with oil or aerosol particles can thus be observed via the window of the adapter housing and subsequently analyzed. Reference is made in this connection to the disclosure of DE 10 2006 023 714 B4, which is part of this application (and corresponding U.S. Pat. No. 7,712,348 is hereby incorporated by reference in its entirety).

An exemplary embodiment of the present invention is shown in the drawings and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1a is a detail view of an apertured diaphragm of the measuring sensor according to FIG. 1.

DESCRIPTION OF THE PREFERRED EMBODIMENTS

Figure 1:
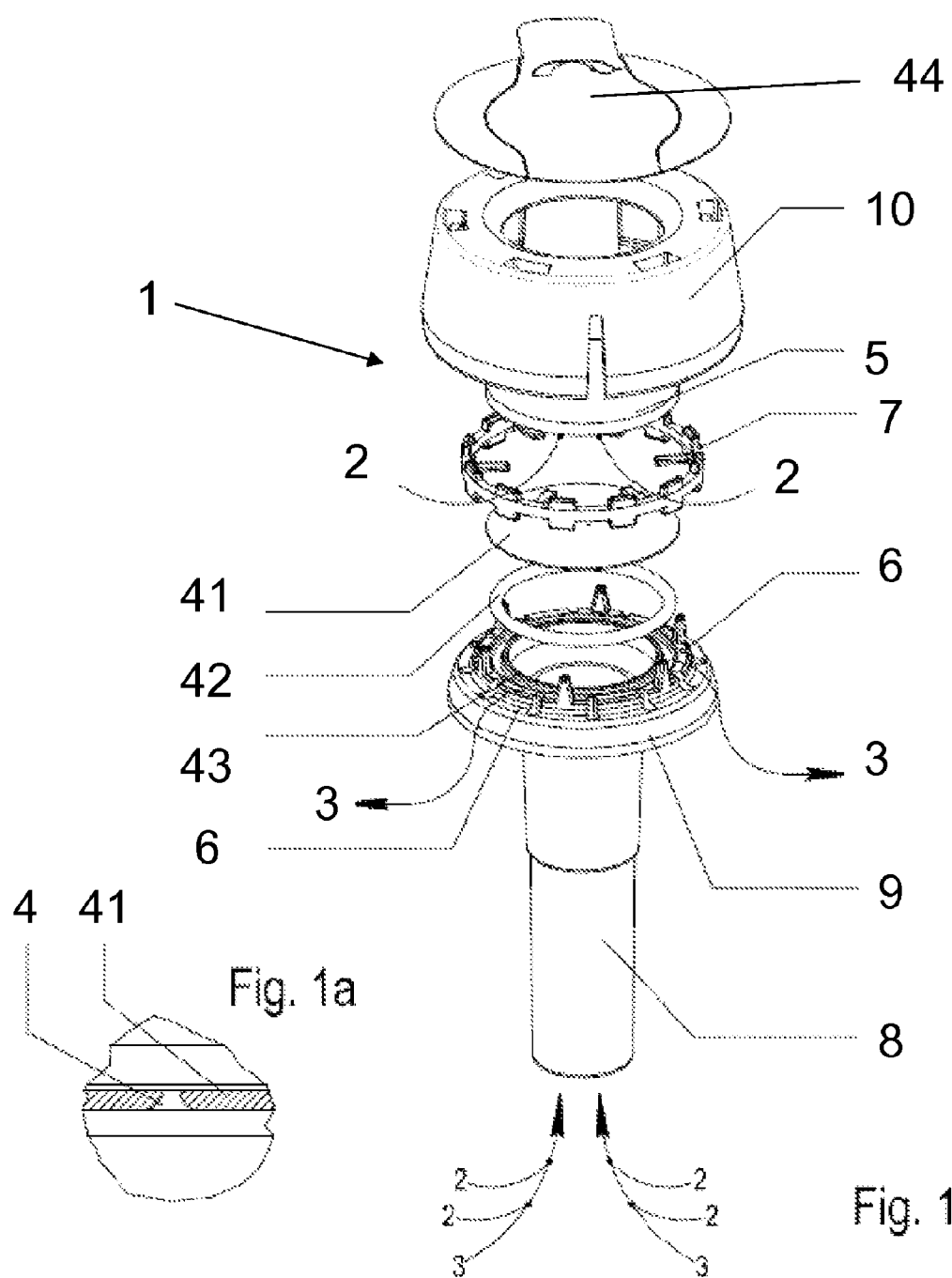
FIG. 1 is a perspective exploded view of a measuring sensor according to the invention.

Referring to the drawings in particular, FIG. 1 schematically shows the design of a measuring sensor 1 for gas analysis. The gas 3 arriving from the gas source, which is not shown more specifically and is loaded with oil particles 2, reaches, via a gas inlet duct 8, a perforated plate 41, which is provided with a plurality of micronozzles 4, FIG. 1a, and is deflected at a transparent deflector 5 at right angles to the inflow direction. Due to the abruptly changing direction of flow, the oil particles 2 cannot follow the flow any longer and are deposited on the inside of the deflector 5. Deflector 5 is fixed to a measuring sensor housing 9 by means of a snap ring 10. The gas being measured 3 is discharged from the interior space of the measuring sensor housing 9 into the environment via gas outlets 6 arranged over the circumference of the measuring sensor housing 9.

The perforated plate 41 lies on a contact surface 43 of the measuring sensor housing 9 via a sealing ring 42. Deflector 5 is arranged opposite the perforated plate 41 by means of a spacer ring 7. A tear tab 44, which is removed before the analysis of a gas sample so that the deflector 5 becomes visible, is located on the top side of snap ring 10.

FIG. 1a shows a detail of perforated plate 41 with a micronozzle 4.

Figure 2:
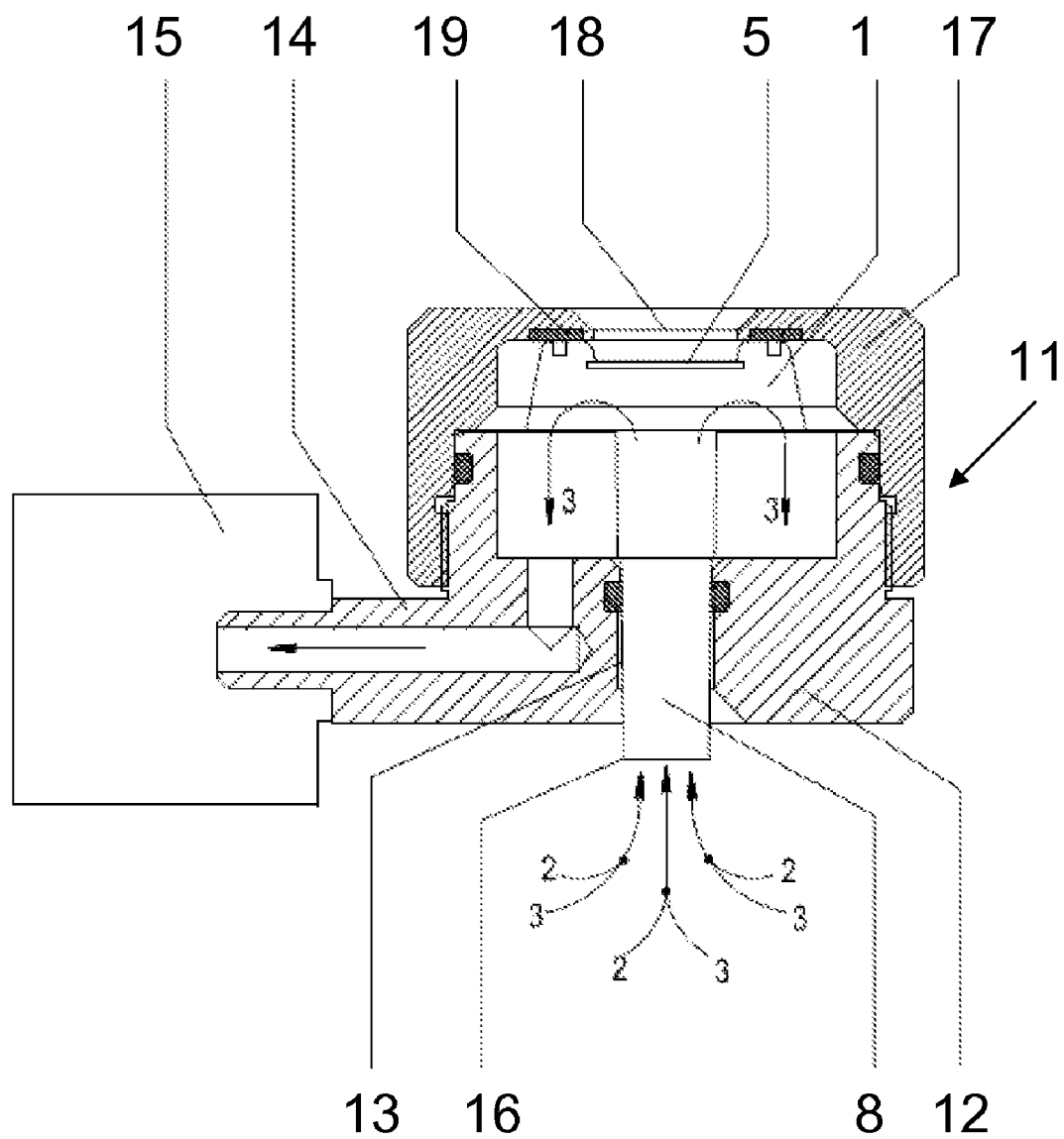
FIG. 2 is a cross sectional view showing an adapter housing in a longitudinal section with the measuring sensor inserted.

FIG. 2 illustrates the design of an adapter housing 11 in a longitudinal section. Adapter housing 11 contains the measuring sensor 1 corresponding to FIG. 1. Adapter housing 11 has a bottom part 12 with a connecting branch 13 for receiving the gas inlet duct 8 of the measuring sensor 1 and a pump port 14 for a gas delivery pump 15. The free end 16 of the gas inlet duct 8 is arranged such that gas 3 can be drawn in from the surroundings of adapter housing 11. Bottom part 12 is closed with a cover 17, and a window 18, which is located opposite the transparent deflector 5 of the measuring sensor 1, is provided on the top side of cover 17. Snap ring 10 of the measuring sensor 1 is pressed onto cover 17 by means of an elastomer ring 19.

The gas 3 to be analyzed, which is loaded with oil particles 2, is drawn in via the gas inlet duct 8 and reaches the gas delivery pump 15 via pump port 14. The oil particles 2 will have been deposited on the deflector 5 of the measuring sensor 1 beforehand With the measuring sensor 1 inserted into the adapter housing, the measuring sensor 1 is encapsulated (or at least partially encapsulated) in the adapter housing 11. The flow path between the gas inlet duct 8 and the gas outlets 6 is sealed to the environment and outlets 6 are sealed in flow connection with pump port 14. With this, a vacuum (low pressure) at pump port 14 results in ambient air being drawn in via the gas inlet duct 8 of the measuring sensor.

While specific embodiments of the invention have been described in detail to illustrate the application of the principles of the invention, it will be understood that the invention may be embodied otherwise without departing from such principles.

APPENDIX

List of Reference Numbers

1 Measuring sensor
2 Oil particle
3 Gas
4 Micronozzle
5 Deflector
6 Gas outlet
7 Spacer ring
8 Gas inlet duct
9 Measuring sensor housing
10 Snap ring
11 Adapter housing
12 Bottom part
13 Connecting port
14 Pump port
15 Gas delivery pump
16 Free end
17 Cover
18 Window
19 Elastomer ring
41 Perforated plate
42 Sealing ring
43 Contact surface
44 Tear tab

What is claimed is:

1. A device for the selective determination of the quantity of oil mist or aerosols in a gas sample, the device comprising:
a measuring sensor with a gas inlet duct, a micronozzle for dispensing a predetermined sample gas flow in a gas inlet chamber and a deflector downstream of the micronozzle for depositing aerosol or oil particles and a gas outlet on a discharge side of the deflector; and
an adapter housing at least partially encapsulating the measuring sensor, the adapter housing having a connecting branch for receiving the gas inlet duct and a pump port connected to the gas outlet establishing a flow connection via the gas inlet duct from the outside of the adapter housing to the pump port, said adapter housing comprising a bottom part with the connecting branch and the pump port and a cover pulled over a free end of the bottom part.

2. A device in accordance with claim 1, wherein a gas delivery pump is connected to the pump port.

3. A device in accordance with claim 1, wherein said cover is provided with a window in an area of said deflector.

4. A device for the selective determination of the quantity of oil mist or aerosols in a gas sample, the device comprising:
a measuring sensor for the selective determination of oil mist or aerosols, the measuring sensor including a gas inlet duct connected to micronozzles for dispensing a predetermined sample gas flow and a deflector downstream of the micronozzles for depositing aerosol or oil particles and a gas outlet on a discharge side of the deflector;
an adapter housing sealing the measuring sensor from the gas inlet duct to the gas outlet such that a created low pressure at the gas outlet results in ambient air being drawn in via the gas inlet duct, said adapter housing comprising a bottom part with a connecting branch and a pump port and a cover pulled over a free end of the bottom part.

5. A device in accordance with claim 4, wherein a gas delivery pump is connected to the pump port.

6. A device in accordance with claim 4, wherein said cover is provided with a window in an area of said deflector.

7. A process for the selective determination of the quantity of oil mist or aerosols in a gas sample, the process comprising:
providing a measuring sensor with a gas inlet duct, a micronozzle for dispensing a predetermined sample gas flow in a gas inlet chamber and a deflector downstream of the micronozzle for depositing aerosol or oil particles and a gas outlet on a discharge side of the deflector;
providing an adapter housing for receiving the measuring sensor, the adapter housing having a connecting branch and a pump port, said adapter housing comprising a bottom part with the connecting branch and the pump port and a cover pulled over a free end of the bottom part; and
inserting the measuring sensor in the adapter housing and sealing the measuring sensor from the gas inlet duct to the gas outlet such that a vacuum at the gas outlet results in ambient air being drawn in via the gas inlet duct.

8. A process in accordance with claim 7, further comprising:

providing a gas delivery pump;

connecting the gas delivery pump to the pump port;

generating a vacuum at the gas outlet using the pump by generating a vacuum at the pump port to draw ambient air in the gas inlet duct.

9. A process in accordance with claim 7, wherein said cover is provided with a window in an area of deflector.

* * * * *